United States Patent [19]

Matsumura et al.

[11] Patent Number: 4,696,822
[45] Date of Patent: Sep. 29, 1987

[54] INSECTICIDAL COMPOSITIONS

[75] Inventors: Takafumi Matsumura, Mishima; Masataka Morishita, Shizuoka, both of Japan

[73] Assignee: Toyo Jozo Company, Ltd., Shizuoka, Japan

[21] Appl. No.: 747,642

[22] Filed: Jun. 21, 1985

[30] Foreign Application Priority Data

Jul. 9, 1984 [JP] Japan ................................. 59-140494

[51] Int. Cl.[4] .......................... A61K 9/04; B01J 13/02
[52] U.S. Cl. ..................... 424/490; 424/84; 424/491; 424/492; 424/496; 424/497; 424/498; 424/DIG. 11
[58] Field of Search ................. 424/16, 17, DIG. 11, 424/84, 490, 496, 497, 498, 491, 492

[56] References Cited

U.S. PATENT DOCUMENTS

| | | | |
|---|---|---|---|
| 2,800,457 | 7/1957 | Green et al. | 428/402.2 |
| 3,436,452 | 4/1969 | Maierson | 264/344 |
| 3,803,045 | 4/1974 | Matsukawa et al. | 424/37 |
| 3,856,699 | 12/1974 | Miyano et al. | 424/38 |
| 3,865,603 | 2/1975 | Szymanski et al. | 424/37 |
| 3,956,172 | 5/1976 | Saeki et al. | 424/37 |
| 4,244,836 | 1/1981 | Frensch et al. | 424/19 |
| 4,273,672 | 6/1981 | Vassiliades | 424/37 |
| 4,303,548 | 12/1981 | Shimazaki et al. | 424/32 |
| 4,479,911 | 10/1984 | Fong | 424/32 |
| 4,586,060 | 4/1986 | Vassiliades | 424/32 |
| 4,609,403 | 9/1986 | Wittwer et al. | 424/37 |

Primary Examiner—Ronald W. Griffin
Attorney, Agent, or Firm—Ladas & Parry

[57] ABSTRACT

An insecticidal composition which contains microcapsules whose core substance is made of 20–85% by weight of an insecticidal ingredient of diazinon or chlorpyrifos and 50% or less by weight of a diluent and wall material made of 10–30% by weight of polycationic water-soluble nitrogen-containing compound and 10% by weight or less of a hardener. The microcapsules may be mixed with coagulation-preventing agent of non-ionic surfactant and water-soluble thickener and then may be shaped into granules.

9 Claims, 1 Drawing Figure

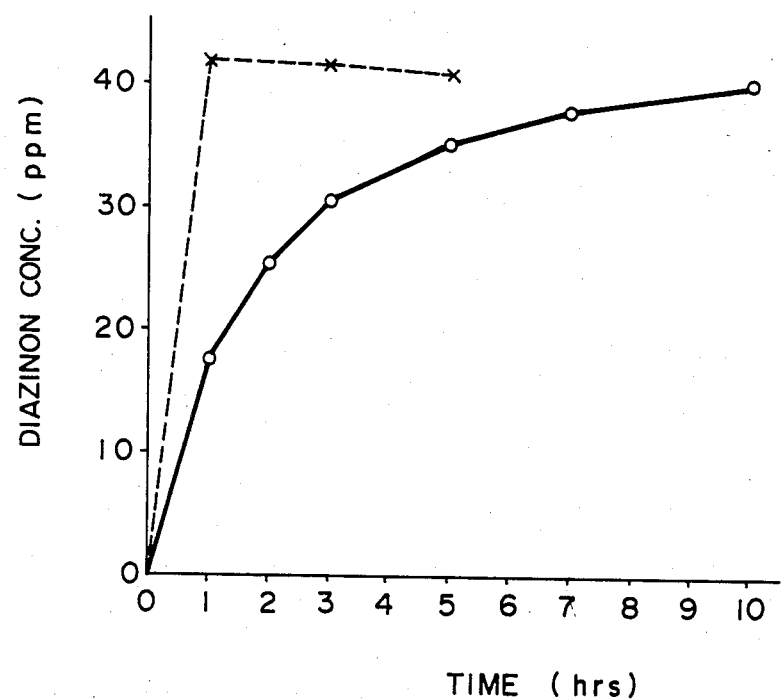

INSECTICIDAL COMPOSITIONS

BACKGROUND OF THE INVENTION

The present invention relates to a novel insecticidal composition comprising a microcapsule wherein diazinon or chlorpyrifos is made a core substance and a polycationic water-soluble nitrogen-containing compound such as gelatin and a hardener are made a wall substance.

Further, it relates to a microcapsule-containing composition comprising microcapsules mentioned above, surfactant to prevent the microcapsules from coagulating each other and a thickener, and also to a novel insecticidal composition consisting of a stable microcapsule-containing composition which is obtained by granulating the microcapsule-containing composition above with a filler.

U.S. Pat. No. 2,800,457 discloses that an oleaginous material is formed into a microcapsule by the complex-coacervation method, and the separation of the microcapsule is conducted by filtration or centrifugal separation method. In general, there is a spray drying process as a method usually used when a material contained in a solution or dispersion is taken out from it as dry powders. However, according to this method, the wall film tends to be porous resulting in a defect that the core material can not be sufficiently formed into capsule, since the drying of the wall film is conducted in a short time. Furthermore, a microcapsule obtained by U.S. Pat. No. 2,800,457 is not a single core but a multiple core and the coagulation among microcapsules is noticed resulting in a defect to cause clogging of spray nozzle when sprayed.

Japanese published examined patent application No. 17433/1973 discloses that the hardening of a gelatin wall substance in the microencapsulation process occurs in an acidic solution; however, the reactivity for hardening reaction in an acidic solution is poor. The microcapsule is unstable and is easily solidified, since a cationic surfactant is used in order to prevent microcapsules produced from coagulation, and the surfactant is left unchanged in the microcapsule after drying. Further, there is reported the use of a cationic or an anionic surfactant to prevent microcapsules from coagulation due to the attachment of them with the rapid increase in the viscosity; however, these surfactants are easily dissociated in an acidic or an alkaline solution and unstable, and cause remarkable foaming. Also there is a fear that an anionic surfactant forms water-insoluble salts in hard water. Though a cationic surfactant has a high sterilizing effect, on the other hand, it reacts with a cellulosic disintegrator used when granulated and solidifies when preserved over a long period of time. The microcapsule has a defect of poor dispersion in water due to a binder and a thickener which are added in order to improve properties of dry powders.

BRIEF SUMMARY OF THE INVENTION

The present invention provides (1) an insecticidal composition consisting of microcapsules wherein diazinon or chlorpyrifos and a diluent are made a core substance and a polycationic water-soluble nitrogen-containing compound and a hardener are made a wall substance;

(2) an insecticidal composition consisting of a microcapsule-containing composition comprising a coagulation-preventing agent to prevent microcapsules from coagulating each other and a water-soluble thickener, in addition to the microcapsules mentioned in above (1); and (3) a microcapsule-containing composition in the granule or shaped by adding a vehicle to the microcapsule-containing composition mentioned in above (2).

The insecticidal composition of the present invention is featured as follows:

(1) The preservability of the action due to the sustained release of insecticidal ingredients of diazinon and chlorpyrifos by making them into microcapsules and the alleviation of the environmental pollution due to the decrease in the amount used and in the odor based upon the above preservability can be effected.

(2) The present microcapsule-containing composition in, for example, granule-like material, is easily prepared by making gelatin microcapsules according to the complex coacervation method and by spray drying in the presence of the coagulation-preventing agent.

(3) The microcapsule-containing composition in the granule form obtained by microcapsulation and granulation is useful in handling and safety for skin contact.

(4) When compared with microcapsules prepared by using other polymers, the gelatin microcapsules can be easily controlled in the release rate of the effective ingredient contained in the microcapsules by adjusting the amount of gelatin and hardener, e.g., formaldehyde and other aldehydes.

(5) By spray drying and granulation, there can be obtained an insecticidal composition which consists of a microcapsule-containing composition in the granule form and which is extremely stable for a long time.

(6) By adding a water-soluble thickner and a filler, there can be obtained a satisfactory microcapsule-containing composition (granule); further, by using them along with a nonionic surfactant, there can be obtained a stable dispersion of a microcapsule-containing composition when used as an aqueous suspension.

(7) A stable dispersion of microcapsule substance can be obtained by adding a diluent to the insecticidal ingredient of diazinon or chlorpyrifos.

BRIEF DESCRIPTION OF THE DRAWING

The drawing shows a graph which represents the gradual release of an insecticidal ingredient, diazinon. In this graph, —o— represents the granule of the diazinon-containing microcapsule of the present invention and —x—, a diazinon-hydrating composition on the market.

DETAILED DESCRIPTION

The most preferable mode to obtain the composition aimed at by the present invention is the coacervation-forming method [U.S. Pat. Nos. 2,800,457 and 2,800,458: H. G. Bungenbergde Jong (Leiden), H. R. Kruyt (Utrecht) "Kolloid Reitshriff. Vol. 50, 1930, p.39: Trans. Fara. Soc., Vol. 46, 1959, p. 310: The Theorey of Coacervation" By C. H. Ramford and H. Tompa. For instance, under heating condition, an emulsion is formed which contain gelatin as a polycationic water-soluble nitrogen-containing compound, gum arabic as a polyanionic compound and diazinon or chlorpyrifos or a diluted solution thereof; then, after diluting the emulsion with warm water, the coacervation is formed while cooling. After that, the addition of the coagulation-preventing agent of a nonionic surfactant and the hardener, and the pH adjustment under alkaline condition, for instance, at pH=9 or higher, are conducted in this order, until microcapsules containing the insecticide aimed at are obtained. Alternatively, the treatment is conducted in the order of addition of the hardener, pH adjustment and the addition of the nonionic surfactant. Then, these microcapsules are recovered by decantation; after this is added to a solution of a water-soluble thickener, the mixture is sprayed to obtain a microcapsular composition, for example, granular-shaped microcapsules. Further, this microcapsular composition is preferably shaped by adding a vehicle thereto in accordance with a known granulation means, for instance, with a cylindrical granulator to obtain a microcapsular composition in the granular form.

Diazinon (formula 1) and chlorpyrifos (formula 2) which are the insecticidal ingredients of the insecticidal composition of the present invention are represented by the following formulas:

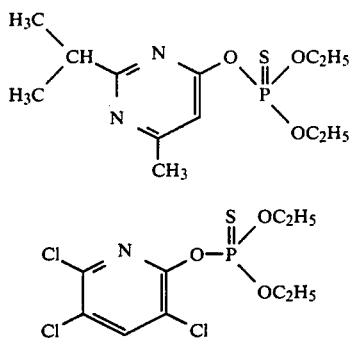

The effective ingredient in the insecticidal composition is 20 to 85 wt. %, preferably 40 to 80 wt. %, based on the total weight of the microcapsule. When its amount is less than 20 %, the revelation of the effect aimed at is poor and there is a problem in the effectiveness.

As the diluent used for the insecticidal composition of the present invention, there are illustrated liquid paraffin containing more volatile component; animal and vegetable oils such as olive oil, rape seed oil, castor oil, sesame oil and whale oil; neutral oils such as Miglol and Neobei; petroleum-orinated organic solvents such as toluene, xylene, benzene and others. The amount of the diluent to be added is 50 wt. % or less, preferably 20 to 50 wt. % based on the total weight of the composition.

As the polycationic water-soluble nitrogen-containing compound which is the wall substance of the microcapsules used for the insecticidal composition of the present invention, for example, proteins such as gelatin, derivatives thereof, casein, albumin and soluble collagen are usually used; the amount thereof to be used is 10 to 30 wt. % based on the total weight of the insecticide composition from the viewpoint of gradual release of the insecticidal ingredient aimed at by the present invention. In addition, a polyanionic compound is used for such a microcapsule formation; there is usually used a compound having a base in the molecule such as, for example, gum arabic, sodium alginate, carrageenan or carboxymethyl cellulose.

As the hardener used when a microcapsule is prepared by coacervation in the present invention, there can be used various known hardeners such as formaldehyde, glutaraldehyde and glyoxal. The amount of the hardener to be used is 10 % by weight or less based on the total weight of the composition from the viewpoint of gradual release of the insecticidal ingredient.

The size of the microcapsule used for the insecticidal composition of the present invention and prepared by coacervation is 5 to 100 microns, preferably 10 to 50 microns.

The coagulation-preventing agent in the insecticidal composition of the present invention is a nonionic surfactant having an HLB of 10-20, preferably a polyoxyethylene sorbitan fatty acid ester having an HLB of 15-20. Its amount is 0.25 to 5 % by weight, preferably 0.25 to 2 % by weight from the viewpoint of the preventing coacervations from coagulating each other and the dispersability of the spray-dried granules in water. Though an amount thereof exceeding this level may be used, there is no meaning of technical effectiveness.

Those nonionic surfactants include, for example, polyoxyethylene (POE) aliphatic alcohol ethers [for example, EMULGEN 106 (POE lauryl alcohol ether: HLB 10.5), EMULGEN 108 (POE lauryl alcohol ether: HLB 12.1), EMULGEN 220 (POE cetyl alcohol ether: HLB 14.2), EMULGEN 408 (POE oleyl alcohol ether: HLB 10.0), Brij 35 (POE(23) lauryl alcohol ether: HLB 16.9), Brij 78 (POE(20) stearyl alcohol ether: HLB 15.3), Brij 98 (POE(120) oleyl alcohol ether: HLB 15.3) and EMULGEN 340 (POE stearyl ether: HLB 17.3) manufactured by Kao Atlas Co., Ltd.; NONIO-LIGHT AL-11 (POE lauryl ether: HLB 14.0) and NONIO-LIGHT AO-20 (POE oleyl ether: HLB 15.4) manufactured by KYOEISHA CHEMICAL CO., LTD.; NIKKOL BB-20 (POE behenyl ether: HLB 17), NIKKOL BL-9EX, BO-10 TX, BC 15 TX and BH 5 manufactured by NIKKO CHEMICALS CO., LTD.; EMALEX BA 10 (POE butyl alcohol ether: HLB 16.9), EMALEX BA 15 (POE butyl alcohol ether: HLB 18.7), EMALEX 130 (POE cetyl alcohol ether: HLB 16.0), EMALEX 100 (POE cetyl alcohol ether: HLB 14.5), EMALEX 550 (POE oleyl alcohol ether: HLB 18.2) and EMALEX 700 (POE lauryl alcohol ether: HLB 16.7)manufactured by NIHON EMULSION CO., LTD.; NONION E-213 (POE oleyl alcohol ether: HLB 13.6), NONION E-220 (POE oleyl alcohol ether: HLB 15.3), NONION P-225 (POE cetyl alcohol ether: HLB 16.4), NONION S-215 (POE stearyl alcohol ether: HLB 14.2) and NONION T-208.5 (POE tridecyl alcohol ether: HLB 13.0) manufactured by NIPPON OIL AND FATS CO., LTD.; LIPONOX OCS (POE alkyl ether: HLB 15.0), LIPONOX LCR (POE alkyl ether: HLB 16.2) and LIPONOX (POE alkyl ether: HLB 14.3) manufactured by Lion Fat & Oil Co., Ltd.; Adekatol SO-120 (POE secondary straight chain alcohol ethoxylate), Adekatol SO-145 (POE secondary straight chain alcohol ethoxylate), Adekatol LO-9 (POE primary straight chain alcohol ethoxylate), Adekatol LO-12 (POE primary straight chain alcohol ethoxylate) and Adekatol LO-15 (POE primary straight chain alcohol ethoxylate) manufactured by ASAHI DENKA KOGYO K. K.; and the like], POE alkyl aryl ethers [for example, EMULGEN 810 (POE octyl phenyl ether: HLB 13.1), EMULGEN 911 (POE nonyl phenyl ether: HLB 13.7), EMULGEN 930 (POE nonyl phenyl ether: HLB 15.1) and EMULGEN 950 (POE nonyl phenyl ether: HLB 18.2) manufactured by Kao Atlas Co., Ltd.; NONIO-LIGHT PO-9 (POE octyl phenyl ether: HLB 13.2) and NONIO-LIGHT PA-15 (POE alkyl phenyl ether: HLB 14.3) manufactured by KYOEISHA CHEMICAL CO., LTD.; EMALEX NP-15 (POE alkyl phenol ether: HLB 13.2) and EMALEX OP-25

(POE alkyl phenol ether: HLB 15.8) manufactured by NIHON EMULSION CO., LTD.; NONION NS-215 (POE nonyl phenol ether: HLB 15.0), NONION NS-220 (POE nonyl phenol ether: HLB 16.0), NONION HS-212 (POE octyl phenol ether: HLB 14.4) and NONION HS-220 (POE octyl phenol ether: HLB 16.2) manufactured by NIPPON OIL AND FATS CO., LTD.; LIPONOX NCM (POE alkyl phenol ether: HLB 14.5), LIPONOX NCN (POE alkyl phenol ether: HLB 14.8) and LIPONOX NCO (POE alkyl phenol ether: HLB 15.0 manufactured by Lion Fat & Oil Co., Ltd.; Nenidet P-40 (POE alkyl aryl ether) manufactured by Shell Co.; Triton X-100 (POE alkyl aryl ether) manufactured by Rohm & Haas Co.; NIKKOL NP-10, NP-18TX, NP-20 and OP-40 manufactured by NIKKO CHEMICALS CO., LTD.; and the like], POE fatty acid esters [for example, EMANON 1112 (POE monolaurate: HLB 13.7), EMANON 4115 (POE monooleate: HLB 13.4), Myrj 45 (POE(8) stearate: HLB 11.1), Myrj 52 (POE(40) stearate: HLB 16.9) and Myrj 53 (POE(50) stearate: HLB 17.9) manufactured by Kao Atlas Co., Ltd.; NONIO-LIGHT S-100 (POE stearate: HLB 15.6) and NONIO-LIGHT T-40 (POE tall oil fatty acid ester: HLB 11.5) manufactured by KYOEISHA CHEMICAL CO., LTD.; EMALEX 202 (POE oleate: HLB 15.1), EMALEX 203 (POE oleate: HLB 17.6), EMALEX 800 (POE monolaurate: HLB 15.8), NONION P-10 (POE monopalmitate: HLB 15.7), NONION S-10 (POE monostearate: HLB 15.2), NONION S-40 (POE monostearate: HLB 18.2) manufactured by NIHON EMULSION CO., LTD.; MYL-10 and MYO-10 manufactured by NIKKO CHEMICALS CO., LTD.; and the like], POE sorbitan fatty acid esters [for example, EMASOL 1130 (POE sorbitan monolaurate: HLB 16.3), EMASOL 3130 (POE sorbitan monostearate: HLB 14.9), Tween 20 (POE(20) sorbitan monolaurate: HLB 16.7), Tween 40 (POE(20) sorbitan monopalmitate: HLB 15.6), Tween 80 (POE(20) sorbitan monooleate: HLB 15.0)manufactured by Kao Atlas Co., Ltd.; NONIO-LIGHT TWL-20 (POE(20) sorbitan monolaurate: HLB 16.2) and NONIO-LIGHT TWS-13 (POE(13) sorbitan monostearate: HLB 12.5) manufactured by KYOEISHA CHEMICAL CO., LTD.; SOLGEN TW 20 (POE sorbitan monolaurate: HLB 16.7) and SOLGEN TW 80 (POE sorbitan monooleate: HLB 15.0) manufactured by DAI-ICHI KOGYO SEIYAKU CO., LTD.; NIKKOL TSDL-2020L (POE sorbitan olive fatty acid: HLB 16.5), TL-10 and TO-106 manufactured by NIKKO CHEMICALS CO., LTD.; EMALEX ET-2000 (POE sorbitan laurate: HLB 16.6) manufactured by NIHON EMULSION CO., LTD.; NONION LT-221 (POE sorbitan laurate: HLB 16.7), NONION ST-221 (POE sorbitan stearate: HLB 14.9) and NONION OT-221 (POE sorbitan oleate: HLB 15.0) manufactured by NIPPON OIL AND FATS CO., LTD.; Serben T-20 (POE sorbitan monolaurate: HLB 16.7), Serben T-40 (POE sorbitan monopalmitate: HLB 15.7) and Serben T-80 (POE sorbitan monooleate: HLB 15.0) manufactured by TOHO CHEMICAL INDUSTRY CO., LTD.; and the like], POE sorbitol fatty acid esters [for example, Atlex 1045A (POE sorbitol oleate-laurate: HLB 13.2), Atlex 1196 (POE sorbitol oleate: HLB 11.4), G-1045 (POE sorbitol laurate: HLB 11.5) and G-1441 (POE sorbitol lanolin derivative: HLB 14) manufactured by Kao Atlas Co., Ltd.; NIKKOL TSOL-1020L (POE sorbitol olive fatty acid ester: HLB 16.0) and GL-1 manufactured by NIKKO CHEMICALS CO., LTD.; and the like], POE castor oil derivatives or POE hardened caster oil derivatives [for example, G-1288 (castor oil ethylene oxide adduct: HLB 16.0), G-1295 (hardened castor oil ethylene oxide adduct: HLB 17.5) and G-1292 (hardened castor oil ethylene oxide adduct: HLB 10.8) manufactured by Kao Atlas Co., Ltd.; NIKKOL CO-60TX (POE(60) castor oil: HLB 14.1) manufactured by NIKKO CHEMICALS CO., LTD.; and the like], POE glycerin fatty acid esters [for example, NIKKOL TGSO 215 (POE glycerin vegetable oil fatty acid ester: HLB 14.0), TGSO 220 (POE glycerin vegetable oil fatty acid ester: HLB 15.5), TDGOL-2010 (POE diglycerin olive oil fatty acid ester: HLB 12.5) manufactured by NIKKO CHEMICALS CO., LTD.; and the like], POE lanolin derivatives [for example, G-1790 and G-1795 manufactured by Kao Atlas Co., Ltd.; BWA-5 manufactured by NIHON CHEMICALS CO., LTD.; and the like], POE type nonionic surfactants such as POE alkyl thioethers and POE propylene glycol monofatty acid esters, block type nonionic surfactants having polyoxypropylene blocks and POE blocks [for example, Plurenie L 121 and L 122 manufactured by ASAHI DENKA KOGYO K.K., and the like], polyhydric alcohol type nonionic surfactants which are esters of polyhydric alcohols having 6 or more carbon atoms such as sorbitan, mannitol, sorbitol and cane sugar and higher fatty acids having 12 or more carbon atoms such as lauric acid, palmitic acid, stearic acid, isostearic acid and other fatty acid derived from natural oils and fats, and the like.

The water-soluble thickener used for the insecticidal composition of the present invention includes sodium carboxymethyl cellulose, gum arabic, poly vinyl alcohol, dextrin, crystalline cellulose, carboxyvinyl polymer, methylcellulose, poly vinyl pyrrolidone, hydroxypropyl cellulose and the like. The thickeners mentioned above can be used individually or as a mixture of 2 or more kinds by 5 to 30% by weight based on the total weight of the composition from the viewpoint of the improvement in binding property when granules are formed. In this case, the size of the microcapsule-containing composition in a granular form after spray drying of microcapsule obtained is 50 to 300 microns.

The insecticidal composition of the present invention can be used as a microcapsule-containing composition in the form of granule by further adding a filler to the microcapsule-containing composition mentioned above for granulation. As the filler, there can be illustrated, for example, starch, dextrin, crystalline cellulose, hydroxypropylcellulose carboxymethylcellulose, calcium carboxymethyl cellulose and inorganic salts, for example, sodium carbonate, sodium hydrogencarbonate, calcium carbonate, calcium hydrogencarbonate, sodium hydrogenphosphate, calcium hydrogenphosphate and sodium sulfate. The amount of the filler to be used is 5 to 30% by weight based on 70 to 95% by weight of the dry granule (dry material) of the microcapsule mentioned above.

The present invention will be explained with examples hereinbelow; however, it is not limited to them.

EXAMPLE 1

A mixture of 100 g of diazinon and 20 g of liquid paraffin containing more volatile component was added to 320 cc of a 10% (w/w) aqueous solution of gelatin. After the emulsification to obtain a particle size of 5 to 10 $\mu$, the emulsion was heated up to 50° C., and 320 cc of an aqueous solution of gum arabic having a 10% (w/v) concentration was added to the emulsion while stirring. After sufficient mixing, the mixture was diluted with 1.1 liters of water warmed to 50° C. The diluted liquid obtained was cooled with ice down to a temperature of 5° C. to cause coacervation. After 2 g of a non-ionic surfactant (RHEODOL TW-L 120 ® manufactured by Kao Corporation) was added to the liquid for dispersion, 40 g of a 25% aqueous solution of glutaraldehyde was added thereto. After 1 hour, the pH of the mixture was increased to 9 or more with a 20% aqueous solution of caustic soda. After the temperature was raised again to 50° C. and the stirring was continued for 30 minutes, the temperature was returned to room temperature to obtain a gelatin wall film capsule slurry (microcapsule).

After this capsule slurry was subjected to decantation, 500 cc of a 1% aqueous solution of AVICEL (RC-591 NF) (manufactured by ASAHI CHEMICAL INDUSTRY CO., LTD.) and 500 cc of a 4% aqueous solution of dextrin were added to the slurry to obtain finally a uniform dispersion having a solid content of 10%, from which a microcapsule-containing composition in the granular form was obtained by using a spray drying rotary atomizer (production minor type; manufactured by ASHIZAWA-NIRO ATOMIZER LTD.)

To 100 g of this microcapsule-containing composition was added 10 g of calcium carboxymethyl cellulose. After the mixture was kneaded with 70% ethanol, the material was made into granules having a size of 1.5 mm$\phi \times$5 mm and dried to obtain a microcapsule-containing composition in the granule form.

In order to examine the elusion ability in water (gradual release in water) of the diazinon-containing microcapsule-containing composition (granule), elusion tests were conducted in comparison with a diazinon hydrating composition on the market.

The testing method is as described below. Into a 200 ml beaker was charged each of them by an amount corresponding to 50 mg of the effective ingredient, and 100 ml of water was added thereto. The mixture was stirred at a rate of 100 r.p.m. Sampling was conducted with the passage of time. After the extraction procedure was conducted with n-hexane, the amount of diazinon was measured by gas chromatography. Incidentally, the solubility of diazinon is 40 p.p.m.

From FIG. 1, it is obvious that the microcapsule-containing composition of the present invention is stable also in water and gradually releases effective ingredient.

EXAMPLE 2

To 320 cc of a 10% (w/w) aqueous solution of gelatin was added 120 g of a chlorpyrifos solution in xylene (71.3% w/w). After the emulsification to obtain a particle size of 5–10 $\mu$, this emulsion was diluted by adding 1.1 liters of water warmed to a temperature of 50° C. This diluted liquid was cooled with ice down to a temperature of 5° C. to cause coacervation. After 2 g of RHEODOL TW-L 120 ® (manufactured by Kao Corporation) was added to the liquid for dispersion, 40 g of a 25% aqueous solution of glutaraldehyde was added thereto. After 1 hour, the pH of the mixture was increased to 9 or more with a 20% aqueous solution of caustic soda. After the temperature was raised again to 50° C. and the stirring was continued for 30 minutes, the temperature was returned to room temperature to obtain a gelatin wall film capsule slurry (microcapsule). After this capsule slurry was subjected to decantation, 500 cc of a 1% aqueous solution of AVICEL (RC-591 NF) (manufactured by ASAHI CHEMICAL INDUSTRY CO., LTD.) and 500 cc of a 4% aqueous solution of gum arabic were added to the slurry to obtain a 10% (solid content) homogeneous dispersion, from which a microcapsule-containing composition was obtained by using a spray drying rotary atomizer (production minor type, manufactured by (ASHIZAWA-NIRO ATOMIZER LTD.). To 100 g of this microcapsule-containing composition was added 10 g of fine crystalline cellulose. After the mixture was kneaded with 70% ethanol solution, the material was made into granules having a size of 1.5 mm$\phi \times$5 mm with a cylindrical granulator and dried to obtain a microcapsule-containing composition (granule).

EXAMPLE 3

The diazinon-containing microcapsule-containing composition (granule) in Example 1 and a diazinon-hydrating agent (effective ingredient: 34%) on the market as a comparative were sprayed on specimens, respectively, and the ratios of attached remains of the medicine were measured. The testing method is as mentioned below. Five 20 day seedlings cultivated in a box were transplanted in a 9 cm polyport. After 10 days, a liquid having a 500 ppm concentration of the effective ingredient of the medicine mentioned above was sprayed thereto at a rate of 150 ml/m$^2$. On the day of the spraying and after 1, 3, 5 and 10 days from the spraying, female grown leafhoppers were released and the insecticidal test was conducted. The results are shown in Table 1.

TABLE 1

|  | Insecticidal rate after 24 hours | | | | |
| --- | --- | --- | --- | --- | --- |
|  | 0 | 1 | 3 | 5 | 10 (day) |
| Diazinon made into microcapsule | 100% | 100% | 95% | 95% | 80% |
| Diazinon-hydrating agent | 100% | 60% | 15% | 0% | — |

EXAMPLE 4

The chlorpyrifos-containing microcapsule-containing composition (granule) in Example 2 and chlorpyrifos (trade name: Dursbon ®) (0.5 wt. %) as a comparative were prepared in such a manner that the content of the effective ingredient was 0.5 wt. %. They were uniformly applied on 15 cm $\times$ 15 cm veneer boards at a rate of 50 ml/m$^2$. After air-drying for 2 hours, Blattellas were forced to contact them for 2 hours. The knock down rate with the passage of time and the lethal rate after 3 days were observed. The results are shown in Table 2.

TABLE 2

|  | Lethal rate after 3 days | | |
| --- | --- | --- | --- |
|  | Immediately after the treatment | After 2 weeks | After 4 weeks |
| Microcapsule substance composition of chloropyriphos (granule) | 100% | 100% | 100% |
| Dursbon ® | 100% | 50% | 30% |

EXAMPLE 5

The compositions of various microcapsules-containing compositions (granules) of the present invention are as follows:

(1) Insecticidal ingredient: Diazinon

| Composition | No. 1 | No. 2 | No. 3 |
| --- | --- | --- | --- |
| Diazinon | 60.0 g | 60.0 g | 50.0 g |
| Liquid paraffin containing more volatile component | — | — | 10.0 |
| Formaldehyde | 1.4 | — | — |
| Glutaraldehyde | — | 4.7 | 4.7 |
| Gelatin | 15.0 | 15.0 | 15.0 |
| Gum arabic | — | — | 5.0 |
| Dextrin | 5.0 | 5.0 | — |
| Sodium carboxymethyl cellulose | — | — | 1.25 |
| Polyoxyethylene sorbitan monostearate | 0.25 | 0.25 | 0.5 |

(2) Insecticidal ingredient: Chlorpyrifos

| Composition | No. 1 | No. 2 |
| --- | --- | --- |
| Chlorpyrifos | 60.0 g | 60.0 g |
| Gelatin | 15.0 | 15.0 |
| Formaldehyde | 1.4 | — |
| Glutaraldehyde | — | 4.7 |
| Gum arabic | 10.0 | 5.0 |
| Dextrin | — | 5.0 |
| Sodium carboxymethyl cellulose | — | 0.5 |
| Polyoxyethylene sorbitan monostearate | 1.0 | 0.25 |

What we claim is:

1. An insecticidal composition containing microcapsules each of which comprises a core substance having 20 to 85% by weight of an insecticidal ingredient of diazinon or chlorpyrifos and 50% or less by weight of a diluent and a wall substance having 10 to 30% by weight of a polycationic water-soluble nitrogen-containing compound and 10% by weight or less of a hardener, said composition further containing 0.25–5% by weight of a coagulation-preventing agent of noionic surfactant and 5 to 30% by weight of water-soluble thickener, said percentages being based on the weight of the composition.

2. The composition according to claim 1, wherein said microcapsule is dry.

3. The composition according to claim 1, wherein said diluent is liquid paraffin, an animal or vegetable oil, a neutral oil or a petroleum-originated organic solvent.

4. The composition according to claim 1, wherein said polycationic water-soluble nitrogen-containing compound is gelatin.

5. The composition according to claim 1, wherein said hardener is formaldehyde, glutaraldehyde or glyoxal.

6. The composition according to claim 1, wherein the coagulation-preventing agent is a nonionic surfactant having an HLB of 10 to 20.

7. The composition according to claim 1, wherein the water-soluble thickener is sodium carboxymethyl cellulose, gum arabic, polyvinyl alcohol, dextrin, crystalline cellulose, carboxyvinyl polymer, methyl cellulose, polyvinyl pyrrolidone or hydroxypropyl cellulose.

8. An insecticidal composition according to claim 1 which is in the granule for containing 70 to 95% by weight of the insecticidal composition as defined in claim 6 and 5 to 30% by weight of a filler, said percentages being based on dry weight of the insecticidal composition.

9. The composition according to claim 8, wherein said filler is starch, dextrin, crystalline cellulose, hydroxypropyl cellulose, carboxymethyl cellulose, calcium carboxymethyl cellulose, sodium carbonate, sodium hydrogencarbonate, calcium carbonate, calcium hydrogencarbonate, calcium hydrogenphosphate or sodium sulfate.

* * * * *